United States Patent
Gilliard et al.

(10) Patent No.: US 6,884,457 B2
(45) Date of Patent: Apr. 26, 2005

(54) SYSTEM AND METHOD FOR TREATING ARTICLES WITH FLUIDS

(75) Inventors: Allen Gilliard, Buford, GA (US); Robert Allen Janssen, Alpharetta, GA (US)

(73) Assignee: Novartis AG, Basel (CH)

( * ) Notice: Subject to any disclaimer, the term of this patent is extended or adjusted under 35 U.S.C. 154(b) by 392 days.

(21) Appl. No.: 10/153,037

(22) Filed: May 22, 2002

(65) Prior Publication Data

US 2002/0190407 A1 Dec. 19, 2002

Related U.S. Application Data

(60) Provisional application No. 60/293,026, filed on May 23, 2001, and provisional application No. 60/325,101, filed on Sep. 26, 2001.

(51) Int. Cl.[7] ......................... A61L 27/00; A61L 27/28; B05D 1/36
(52) U.S. Cl. ....................... 427/2.24; 427/2.1; 427/2.3; 427/106; 427/164; 427/209; 427/402; 427/421; 422/300; 134/34; 134/36; 134/42; 134/26; 134/25.4
(58) Field of Search ................................ 427/2.1, 2.24, 427/2.3, 106, 164, 209, 402, 421; 422/300; 134/34, 36, 42, 26, 25.4

(56) References Cited

U.S. PATENT DOCUMENTS

| 5,720,930 A | 2/1998 | Bean ......................... 422/300 |
| 6,695,988 B1 * | 2/2004 | Schlagel et al. ............. 264/2.6 |

FOREIGN PATENT DOCUMENTS

| DE | 42 28 612 C1 | 12/1993 |
| DE | 44 02 906 A1 | 8/1994 |
| DE | 198 42 284 A1 | 3/2000 |
| EP | 0 317 990 B1 | 11/1988 |
| EP | 0 453 232 B1 | 3/1997 |
| EP | 1 070 963 A2 | 6/2000 |
| EP | 0 854 784 B1 | 12/2001 |
| WO | WO 01/32408 A2 | 5/2001 |

OTHER PUBLICATIONS

European Search Report.

* cited by examiner

Primary Examiner—Jennifer Kolb Michener
(74) Attorney, Agent, or Firm—Jian Zhou; Robert Gorman; R. Scott Meece

(57) ABSTRACT

The present invention provides a method for efficiently and uniformly treating articles with two or more fluids without transferring the articles from one container to another container. The method comprises: providing the fluids, one at a time, to treat the articles in a treatment system, wherein the treatment system comprises one or more trays each of which has one or more baskets, each basket capable of holding one article, and wherein said trays are stacked to form a vessel or are stacked and placed within a preformed vessel, said vessel or preformed vessel comprising a first entrance/exit and a second entrance/exit for the fluids; and each time one of the fluids is provided to treat the articles, (a) flushing continuously the articles with the fluid in a first flow direction from the first entrance/exit to the second entrance/exit, (b) reversing the flow direction of the fluid, (c) flushing continuously the articles with the fluid in a second direction from the second entrance/exit to the first entrance/exit for a second period of time, and (d) if necessary, repeating steps (a) to (c) for a desired number of times.

11 Claims, 2 Drawing Sheets

SYSTEM AND METHOD FOR TREATING ARTICLES WITH FLUIDS

This application claims benefit of No. 60/293,026 filed May 23, 2001 and claims benefit of No. 60/325,101 filed Sep. 26, 2001.

This invention relates broadly to methods and systems for treating articles with one or more solutions. In particular, this invention relates to uniformly treating ophthalmic lenses with one or more solutions.

BACKGROUND

Mass production of ophthalmic lenses generally comprises one or more wet treatment processes, in which the ophthalmic lenses are treated with a variety of solutions in a variety of ways to modify the properties of the ophthalmic lenses. For example, contact lenses are typically subjected to extraction processes during the manufacture of the lens in order to remove unpolymerized monomers or macromers from the molded lens, or to hydration processes during the manufacture of the lens in order to remove undesired solvents originating from the polymerization or molding steps. Contact lenses may also be subjected to tinting processes, in which the contact lenses are exposed to a treatment solution (tinting solution) containing a reactive dye in order to impart ultraviolet (UV) light absorbing properties or visible light absorbing properties to the lens. Another example of wet treatment of contact lenses involves exposure of the lens to a monomer solution with graft polymerization being induced to alter the surface properties of the lens. A further example is that contact lenses are subjected to layer-by layer processes (LbL) as disclosed in a pending U.S. patent application Ser. No. 09/199,609 filed on Nov. 25, 1998, now abandoned in order to increase hydrophilic properties of the lenses. LbL processes typically involve consecutively dipping of the lenses into solutions of oppositely charged polyionic materials until a coating of a desired thickness is formed.

In order to efficiently and economically treat lenses with solutions, one may treat many lenses at one time by placing each lens in a compartment within a tray having numerous cavities. Typically, the lenses are confined in wells which can prevent the lenses from inverting or rolling over. Such a tray holding numerous lenses may be immersed in a container holding an extracting solution, a hydrating solution, a rinsing solution, a tinting solution, a monomer grafting solution, or a LbL coating solution in order to efficiently treat many lenses at once. However, there are problems associated with switching from one wet treatment to another. For example, an extraction process may be carried out in a first container having an extracting solution by placing trays holding the lenses. Before rinsing the lenses, the trays may need to be transferred to a second container having a rinsing solution. Significant manual handling of the lens may be required in transferring lenses from one treatment to another. Such operation may not be efficient or cost-effective.

Furthermore, there are problems associated with the lenses resting against the tray compartments or associated with gas bubbles being attached to the lenses. For example, an extended contact period of the lens with the tray causes concentration gradients, resulting in lenses which are non-uniformly tinted or non-uniformly surface-modified. Attached bubbles prevent a treatment solution from contacting all parts of a lens and thereby prevent the lens from being treated uniformly during a washing, extracting, coating, or tinting process.

Thus, there is a need for a method of treating contact lenses with one or more solution in an efficient, economical, uniform manner. There also remains a need for a wet treatment system for contact lenses in which all of wet treatment processes such as extraction, rinsing, hydration, tinting, and coating can be carried without transferring lenses.

An object of the invention is to provide a single system for efficiently and uniformly treating articles with one or more fluids.

Another object of the invention is to provide a method of efficiently and uniformly treating articles with a fluids.

A further object of the invention is to provide a method of sequentially treating articles with two or more fluids without needs for transferring lenses from one container to another container.

SUMMARY OF THE INVENTION

The foregoing and other objectives are achieved by the various aspects of the invention described herein.

The invention, in one aspect, provides a system for efficiently and uniformly treating articles with one or more fluids. The system includes: a vessel that has a first entrance/exit and a second entrance/exit for a fluid; one or more trays each of which has one or more baskets, each basket able to hold one article and each basket having one or more openings to allow the fluid to flow through the trays, wherein the trays are stacked to form the vessel or stacked and placed in the vessel; and a means for generating a continuous flow of a fluid through the trays in a first direction from the first entrance/exit to the second entrance/exit or in a second direction from the second entrance/exit to the first entrance/exit. The flow direction of a fluid can be reversed from one to another in the system of the invention.

In a preferred embodiment, the vessel is formed by assembling the stacked trays with a first plenum having the first entrance/exit and a second plenum having the second entrance/exit with the help of a sealing means for providing air-tight seals between the first plenum and a first tray in the stack under contact, between the second plenum and a last tray in the stack under contact, and between two neighboring stacked trays.

In another preferred embodiment, the tolerance between the size of the trays and the inside dimension of the vessel is sufficiently tight so as to allow the flow of the fluid travel through the cavities of the stack of the trays instead of around them.

In a further preferred embodiment, the vessel comprises two side-by-side compartments, a first compartment having the first entrance/exit and a second compartment having the second entrance/exit.

The invention, in another aspect, provides a method for treating articles with a fluid. The method comprises the steps of: placing the articles in a treatment system, wherein the treatment system comprises one or more trays each of which has one or more baskets, each basket capable of holding one article, and wherein said trays are stacked to form a vessel or are stacked and placed within a preformed vessel, said vessel or preformed vessel comprising a first entrance/exit and a second entrance/exit for the fluids; flushing continuously the articles with the fluid in a first flow direction from the first entrance/exit to the second entrance/exit for a first period of time; reversing the flow direction of the fluid; and flushing continuously the articles with the fluid in a second direction from the second entrance/exit to the first entrance/exit for a second period of time.

In a further aspect, the present invention provides a method for treating lenses with two or more fluids. The method comprises: providing the fluids, one at a time, to treat the articles in a treatment system, wherein the treatment system comprises one or more trays each of which has multiple baskets, each basket capable of holding one article, and wherein said trays are stacked to form a vessel or are stacked and placed within a preformed vessel, said vessel or preformed vessel comprising a first entrance/exit and a second entrance/exit for the fluids; and each time one of the fluids is provided to treat the articles, (a) flushing continuously the articles with the fluid in a first flow direction from the first entrance/exit to the second entrance/exit, (b) reversing the flow direction of the fluid, (c) flushing continuously the articles with the fluid in a second direction from the second entrance/exit to the first entrance/exit for a second period of time, and (d) if necessary, repeating steps (a) to (c) for a desired number of times.

These and other aspects of the invention will become apparent from the following description of the presently preferred embodiments taken in conjunction with the following drawings. The detailed description and drawings are merely illustrative of the invention and do not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Figure 1:
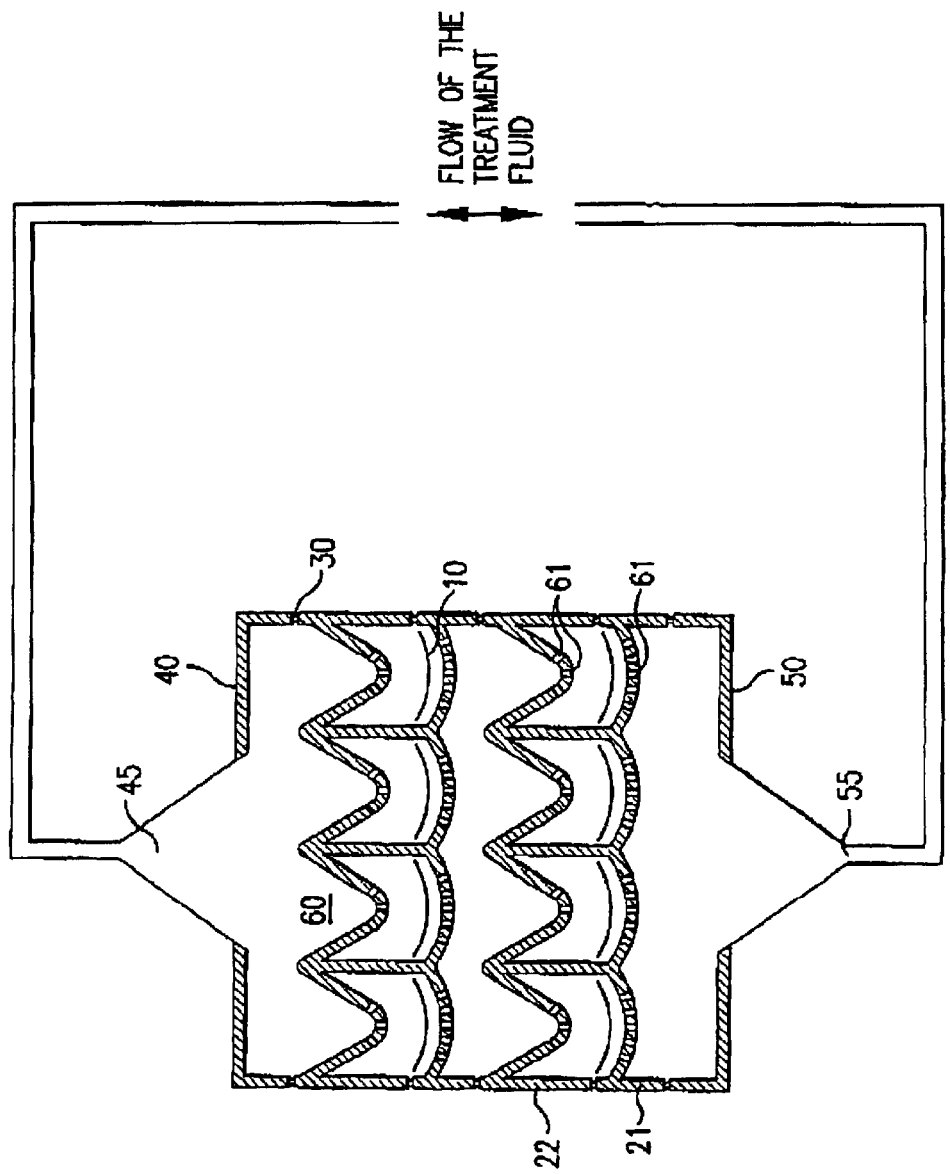
FIG. 1 is a schematic presentation of a tray/vessel system for efficiently and uniformly treating ophthalmic lenses with one or more solutions according to a preferred embodiment of the invention.

In order to enhance the reader's understanding of the invention, select terms will be defined prior to the detailed description of the invention.

An "article", as used herein, refers to ophthalmic lenses and medical devices. While the present invention is discussed with reference to the preferred article of treatment, i.e., ophthalmic lenses, the invention is not limited to the treatment of ophthalmic lenses.

An "ophthalmic lens", as used herein, refers to any lens intended for use in intimate contact with the eye of the user. This includes, without limitation, intraocular lenses, ocular implants, hard contact lenses, and soft contact lenses. The preferred treatment article of the present invention is a contact lens. A contact lens has a posterior (back) surface having a concave curvature and an opposite anterior (front) surface having a convex curvature.

A "medical device" as used herein refers to a device having surfaces that contact tissue, blood, or other bodily fluids of patients. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic lenses.

A "fluid", as used herein, means a gas or liquid intended for contact with an article in order to treat the article. A liquid fluid can be one of solvents such as alcohols, saline solutions, or sterile water, which are intended to clean or rinse the article or to extract chemical species from the article to be treated. A liquid can also be a solution that contains chemical species which are reactive or are intended for reaction with the article. Examples of such chemical species includes, without limitation, reactive dyes (e.g., halotriazine or vinyl sulfone dyes), hydrophilic or hydrophobic monomers, macromers, or polyionic materials.

"Surface modification", as used herein, refers to treating an article to alter its surface properties. For example, the surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or to impart antimicrobial or antifungal properties.

A "monomer" means a low molecular weight compound that can be polymerized. Low molecular weight typically means average molecular weights less than 700 Daltons. Examples of monomers include, but are not limited to, HEMA (2-hydroxyethyl methacrylate), chlorosilanes, methoxysilanes, methacryloxyethyltrimethoxylsilane, methacryoxyethylmethyldimethoxysilane, methacryloxyethyldimethylethoxysilane, methacryloxypropylmethyldichlorosilane, methacryloxypropyltrichlorosilane, and 3-methacryloxypropyldimethylchlorosilane.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Tinting", as used herein, refers to treating an article to change the article's light-absorbing properties. For example, the tinting of a contact lens includes, without limitation, reducing the ultraviolet, infrared, or visible light transmission through the contact lens.

"Hydration", as used herein, refers to a process in which undesired solvents originating from the polymerization or molding steps are removed from articles.

"Extraction", as used herein, refers to a process in which unpolymerized monomers or macromers are removed from molded articles.

"LbL coating", as used herein, refers to a layer-by-layer ("LbL") deposition of polyelectrolytes on an article. Any suitable LbL polyelectrolyte deposition techniques can be used in the LbL coating. For example, a pending U.S. patent application Ser. No. 09/199,609, filed on Nov. 25, 1998, discloses a LbL polyelectrolyte deposition technique that involves consecutively dipping a substrate into oppositely charged polyionic materials until a coating of a desired thickness is formed.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly (vinylbenzyltriamethylamine) (PVBT), polyaniline (PAN or PANI) (p-type doped) [or sulphonated polyaniline], polypyrrole (PPY) (p-typed doped), poly(pyridinium acetylene).

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly (styrene sulfonate) (SPS) and poly(sodium styrene sulfonate) (PSSS).

A "basket" refers to an assembly that comprises two or more members and a means for securing the members together to form a cavity for receiving a medical device, all members having openings for allowing fluid to pass through the basket while the medical device is in place. Openings can have any shapes. Preferably, a basket comprises a first member and a second member and has a percentage of opening surface over total surface being at least 25%. The shape of a basket is preferably designed to accommodate the shape of a medical device to be held.

A basket for holding an ophthalmic lens comprises a pair of mating members (i.e., a female member and a male member), and a means for securing the members together to form a cavity for receiving the ophthalmic lens. Such cavity inhibits inversion or rolling over of the ophthalmic lens when an ophthalmic lens is in place. Preferably, the male member can be inserted within the female member such that there is clearance for an ophthalmic lens between the two members, yet not enough so that the ophthalmic lens can invert or roll over. More preferably, there are through-holes in the centers of the female and male members, and the sharp edges available for an ophthalmic lens to contact are radial lines without nodes. Such radial lines without nodes can provide a minimal surface available for an ophthalmic lens to temporarily or permanently contact.

A "tray", as used herein, refers to a assembly holding a plurality of baskets, each basket for holding an article. A plurality of baskets can be intrinsic parts of a tray, or can be assembled together by one or more support members. "Support members" means any structural elements which together can hold a plurality of baskets. A plurality of baskets can be arranged in any way, for example, in rows or a matrix, in a tray.

Preferably, a tray comprises a first tray portion which holds the first members of a plurality of baskets, a second tray portion which holds the second members of the plurality of basket and a securing means for securing the first and second tray portions together to form the plurality of baskets for holding a plurality of medical devices.

A tray for holding a plurality of ophthalmic lenses preferably comprises a first portion which holds the male members of a plurality of baskets, a second tray portion which holds the female members of the plurality of basket and a securing means for securing the first and second tray portions together to form the plurality of baskets. Each of the male members can be inserted within one female member such that there is clearance for an ophthalmic lens between the two members, yet not enough so that the ophthalmic lens can invert or roll over when emplaced therein.

One embodiment of the invention is a system for efficiently and uniformly treating articles with one or more fluids. The system includes one or more trays, a vessel, and a pumping means for generating a continuous flow of a fluid through the trays in one of two directions. Each tray has a plurality of baskets that can hold one or more articles. Each basket has one or more openings that allow the fluid to flow through the trays. The vessel comprises a first entrance/exit and a second entrance/exit for the fluids and holds the trays. The pumping means can reverse the flow direction of a fluid from one to another in the system of the invention.

One preferred embodiment is schematically illustrated in FIG. 1. The system includes a stack of trays containing lenses 10 under treatment, a first plenum 40 having a first entrance/exit 45 and a second plenum 50 having a second entrance/exit 55. Each of the trays comprises a male portion 21 and female portion 22. The male portion and the female portion assembled to form a plurality of baskets 60 with openings 61. The first entrance/exit faces the back surface of lenses 10 and the second entrance/exit faces the front surface of the lenses 10. There are liquid-tight seals at each of union points 30 between two neighboring stacked trays, between the first plenum 40 and a first tray under contact, and between the second plenum 50 and a last tray under contact. The first plenum, the stack of trays and the second plenum are assembled into a vessel in which the flow path of a treatment solution is from one of the two entrance/exit to the other through the cavities of the stack of lens-holding trays. Continuous flow and flow direction of a fluid is controlled by a means such as a pump (not shown). It should be understood that the stack of trays can be replaced by one single tray.

Figure 2:
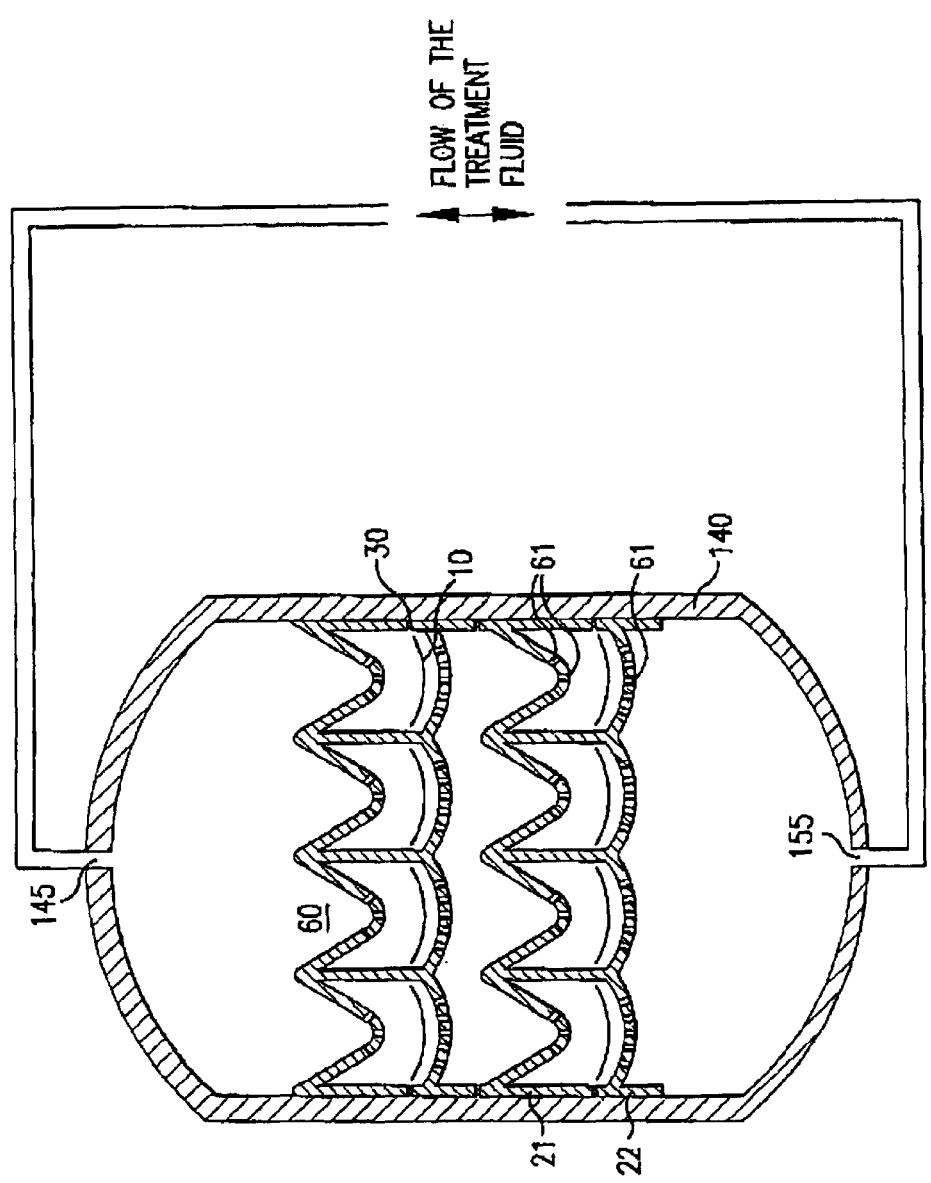
FIG. 2 is a schematic presentation of a tray/vessel system for efficiently and uniformly treating ophthalmic lenses with one or more solutions according to a preferred embodiment of the invention.

Another preferred embodiment is schematically illustrated in FIG. 2. The system includes a stack of trays containing lenses 10 under treatment and a vessel 140 having a first entrance/exit 145 and a second entrance/exit 155. Each of the trays comprises a male portion 21 and female portion 22. The male portion and the female portion assembled to form a plurality of baskets 60 with openings 61. The stack of trays are placed in the vessel 140 in a way that the first entrance/exit faces the back surface of the lenses 10 and that the tolerance between the size of the trays and the inside dimension of the vessel 140 is sufficiently tight enough to allow the flow of fluid to travel through the cavities of the stack of lens-holding trays instead of around them. Continuous flow and flow direction of a fluid is controlled by a means. It should be understood that the stack of trays can be replaced by one single tray.

A further preferred embodiment is that the vessel has two side-by-side compartments, a first compartment having the first entrance/exit and a second compartment having the second entrance/exit. Each of the compartments can be a sub-vessel similar to that shown in FIG. 1 or FIG. 2. Each compartment contains a stack of trays. Two stacks of trays are placed in the vessel in a way that both entrances/exits face the back surface of the lenses. There is a fluid channel between the two compartments, which allows the fluid to travel first through the cavities of one stack of lens-holding trays and then through the other stack of trays. Continuous flow and flow direction of a fluid is controlled by a means such as a pump.

Another further preferred embodiment is that there is a dividing means for dividing each of the stack of the trays into a first portion and a second portion and for forcing a fluid to travel first through a stack of the first (second) tray portions and then through a stack of the second (or first) tray portions. The first entrance/exit and the second entrance/exit are located on the same end of the vessel but divided by the dividing means. A dividing means can be sealing joining walls between one end of the vessel and a first tray in the stack under contact and between two neighboring stacked trays. In this preferred embodiment, a fluid can travel first through a stack of the first (second) tray portions in a direction from a first tray to a last tray and then through a stack of the second (or first) tray portion in a direction from the last tray to the first tray.

The tray/vessel system of the invention can offer several benefits in the manufacture of articles, preferably ophthalmic lenses, more preferably contact lenses. First, extraction, rinsing, hydration, tinting, and coating could be carried out in the same tray and vessel. Second, the flow of fluid through the cavities containing articles (in particular the action of the pulse-jet) removes any gas bubbles that may have attached to the lenses ensuring that a treatment solution is in contact with all parts of the lens. Third, the action of the flow provides a natural cleaning action to the lens, removing any particles that may have stuck to the surface of the lens. Forth, the lens is constantly exposed to fresh solution.

Another embodiment of the invention is a method for treating articles, preferably ophthalmic lenses, more preferably contact lenses, with a fluid, the method comprising the steps of: placing the articles in a treatment system, wherein the treatment system comprises at least two trays each of which has multiple baskets, each basket capable of holding one article, and wherein said trays are stacked to form a vessel or are placed within a preformed vessel, said vessel or preformed vessel comprising a first entrance/exit and a second entrance/exit for the fluids; flushing continuously the articles with the fluid in a first flow direction from the first entrance/exit to the second entrance/exit for a first period of time; reversing the flow direction of the fluid; and flushing continuously the articles with the fluid in a second direction from the second entrance/exit to the first entrance/exit for a second period of time.

The tray/vessel system and method for treating ophthalmic lenses can find particular use in sequential treatments of the articles with two or more fluids. For example, an extraction, an rinsing, and coating processes can be performed sequentially just by switching sequentially from a first treatment solution to a second treatment solution to a third treatment solution, without moving/transferring trays. By sequentially performing treatment process in the same tray/vessel system the amount of lens handling work can be reduced, resulting in a reduction of product lost due to physical damage done to some lenses.

The tray/vessel system and method for treating ophthalmic lenses can find particular use in a surface modification process such as LbL coating and grafting of monomers or macromers onto articles. One problem often encountered in a LbL coating or grafting process is the adhesion of articles to baskets so that articles are not treated uniformly. Such adhesion problem can be minimized by alternatively flushing with a treatment solution in two directions. When the fluid flows in one direction, a first surface of an article is forced by the fluid flow against a first member of a basket. When the fluid flows in the other direction, the article can be dislodged by the fluid flow from the first member of the basket and be forced against a second member of the basket. By changing the flow direction of the fluid, the article under treatment always has a surface which is not adhered to the basket and is completely exposed to the fresh treatment solution.

A further embodiment of the invention is a method for treating articles, preferably ophthalmic lenses, more preferably contact lenses, with two or more fluids. The method comprises: providing the fluids, one at a time, to treat the articles in a treatment system, wherein the treatment system comprises at least two trays each of which has multiple baskets, each basket capable of holding one article, and wherein said trays are stacked to form a vessel or are placed within a preformed vessel, said vessel or preformed vessel comprising a first entrance/exit and a second entrance/exit for the fluids; and each time one of the fluids is provided to treat the articles, (a) flushing continuously the articles with the fluid in a first flow direction from the first entrance/exit to the second entrance/exit, (b) reversing the flow direction of the fluid, (c) flushing continuously the articles with the fluid in a second direction from the second entrance/exit to the first entrance/exit for a second period of time, and (d) repeating steps (a) to (c) for a desired number of times.

In a preferred embodiment, the method for treating articles with two or more fluids further comprises, before switching from a previous fluid to a new fluid, the steps of draining the previous fluid from the system, purging the previous fluid with the new fluid, and priming the system with the new fluid.

What is claimed is:

1. A method for treating articles, said articles being ophthalmic lenses or medical devices, the method comprising:
   (1) providing two or more fluids, one at a time, to treat the articles, said articles being ophthalmic lenses or medical devices, in a treatment system, wherein the treatment system comprises one or more trays each of which has one or more baskets, each basket capable of holding one article, and wherein said trays are used to form a vessel or placed within a preformed vessel, said vessel or preformed vessel comprising a first entrance/exit and a second entrance/exit for the fluids; and
   (2) each time one of the fluids is provided to treat the articles,
      (a) flushing continuously the articles with the fluid in a first flow direction from the first entrance/exit to the second entrance/exit,
      (b) reversing the flow direction of the fluid,
      (c) flushing continuously the articles with the fluid in a second direction from the second entrance/exit to the first entrance/exit for a second period of time, and
      (d) optionally, repeating steps (a) to (c) for a desired number of times.

2. A method of claim 1, further comprising, before switching from a previous fluid to a new fluid, the steps of:
   i) draining the previous fluid from the system;
   ii) purging the previous fluid with the new fluid; and
   iii) priming the system with the new fluid.

3. A method of claim 2, wherein the articles are ophthalmic lenses.

4. A method of claim 3, wherein the ophthalmic lenses are contact lenses.

5. A method of claim 4, wherein a first face of each of the contact lenses faces the first flow direction of the fluid and a second surface of each of the contact lenses faces the second flow direction of the fluid.

6. A method of claim 5, wherein one of the fluids is an extracting solution, a hydrating solution, a rinsing solution, a tinting solution, a monomer grafting solution, or a LbL coating solution.

7. A method for treating articles, said articles being ophthalmic lenses or medical devices, with a fluid, the method comprising the steps of:

(1) placing the articles, said articles being ophthalmic lenses or medical devices, in a treatment system, wherein said system comprises one or more trays each of which has one or more baskets, each basket capable of holding one article, and wherein said trays are stacked to form a vessel or are placed within a preformed vessel, said vessel or preformed vessel comprising a first entrance/exit and a second entrance/exit for the fluids;

(2) flushing continuously the articles with the fluid in a first flow direction from the first entrance/exit to the second entrance/exit for a first period of time;

(3) reversing the flow direction of the fluid; and (4) flushing continuously the articles with the fluid in a second direction from the second entrance/exit to the first entrance/exit for a second period of time.

8. A method of claim 7, further comprising repeating steps (2) to (4) for a desired number of times.

9. A method of claim 8, wherein the articles are ophthalmic lenses.

10. A method of claim 9, wherein the ophthalmic lenses are contact lenses.

11. A method of claim 10, wherein a first face of each of the contact lenses faces the first flow direction of the fluid and a second surface of each of the contact lenses faces the second flow direction of the fluid.

* * * * *